(12) United States Patent
Wieland-Berghausen et al.

(10) Patent No.: US 8,236,851 B2
(45) Date of Patent: Aug. 7, 2012

(54) MICROSPHERULES CONTAINING A PLEUROMUTILIN DERIVATIVE

(75) Inventors: Susanne Christine Wieland-Berghausen, Lörrach (DE); Ferenc Jozsef Rakoczi, Muttenz (CH); Brigitte Monika Cron-Eckhardt, Binningen (CH)

(73) Assignee: Novartis AG, Basel (CH)

( * ) Notice: Subject to any disclaimer, the term of this patent is extended or adjusted under 35 U.S.C. 154(b) by 243 days.

(21) Appl. No.: 10/496,610

(22) PCT Filed: Nov. 27, 2002

(86) PCT No.: PCT/EP02/13388
§ 371 (c)(1),
(2), (4) Date: Sep. 13, 2004

(87) PCT Pub. No.: WO03/045354
PCT Pub. Date: Jun. 5, 2003

(65) Prior Publication Data
US 2005/0070486 A1  Mar. 31, 2005

(30) Foreign Application Priority Data
Nov. 28, 2001 (EP) .................................. 01128276

(51) Int. Cl.
*A01N 37/08* (2006.01)
*A61K 31/215* (2006.01)
*A61K 9/16* (2006.01)
(52) U.S. Cl. .................... 514/511; 424/487; 424/501
(58) Field of Classification Search .................. 514/365, 514/54, 511; 424/487, 501
See application file for complete search history.

(56) References Cited

U.S. PATENT DOCUMENTS

| 3,919,290 A | 11/1975 | Egger | |
| 3,987,194 A * | 10/1976 | Baughn et al. | 514/252.12 |
| 4,086,359 A | 4/1978 | Dursch | |
| 4,675,330 A | 6/1987 | Berner | |
| 5,460,817 A * | 10/1995 | Langley et al. | 424/408 |
| 5,496,565 A * | 3/1996 | Heinze et al. | 424/502 |
| 5,578,585 A * | 11/1996 | Matous et al. | 514/58 |
| 5,607,697 A * | 3/1997 | Alkire et al. | 424/495 |
| 5,614,222 A * | 3/1997 | Kaplan | 424/489 |
| 5,624,710 A * | 4/1997 | Grabitz | 427/212 |
| 5,948,431 A * | 9/1999 | Lavery | 424/438 |

FOREIGN PATENT DOCUMENTS

| DE | 21 05 039 | 8/1971 |
| EP | 0 165 577 | 12/1985 |
| EP | 0 658 313 | 6/1995 |
| EP | 0 707 798 | 4/1996 |
| EP | 0153277 | 8/1998 |
| WO | WO-9801127 | 1/1998 |
| WO | WO 01/37828 | 5/2001 |

OTHER PUBLICATIONS

Database WPI Section Ch, Week 199123, Derwent Publications, Ltd. Class B05, AN 1991-168376 XP002197610 (1991).
Dataase WPI, Section Ch, Week 198812, Derwent Publications, Ltd, Class A96, An 1988-080733, XP002198060 & JP 63 033330, (1988).

* cited by examiner

*Primary Examiner* — Shaojia Anna Jiang
*Assistant Examiner* — Jonathan S Lau

(57) ABSTRACT

The provision of animal feed pellets is described, which pellets comprise, as antibiotic, a pleuromutilin derivative is stabilized form, namely in the form of microspherules. The pleuromutilin derivatives in question have the general formula (I) wherein $R_1$ is ethyl or vinyl, there is either a double bond or a single bond between carbon atoms 1 and 2, Ra and Rb are each independently of the other hydrogen or halogen, and T is a short or long-chain organic radical.

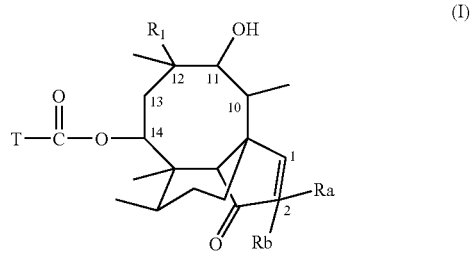

2 Claims, No Drawings

MICROSPHERULES CONTAINING A PLEUROMUTILIN DERIVATIVE

The present application is a §371 of PCT/EP02/13388, filed 27 Nov. 2002, which claims the benefit of EP Application Serial Number 01128276, filed 28 Nov. 2001, the entirety of each hereby incorporated by reference.

The present invention relates to the provision of animal feed pellets comprising, as antibiotic, a pleuromutilin derivative in stabilised form. The invention relates also to the preparation of stabilised pleuromutilin derivatives, to the preparation of said animal feed pellets and to the use thereof in a method of controlling infectious diseases in animals.

Pleuromutilin derivatives are understood hereinbelow to be compounds that contain, as characterising feature, the macrocyclic fragment of formula I below

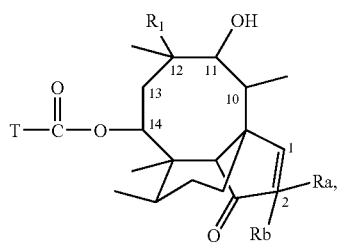

wherein $R_1$ is ethyl or vinyl, there is either a double bond or a single bond between carbon atoms 1 and 2, Ra and Rb are each independently of the other hydrogen or halogen, and T is a short or long-chain organic radical that preferably is as defined hereinbelow.

In some publications, the terms pleuromutilins, valnemulins, tiamulins and mutilins are used synonymously. The term pleuromutilins will be consistently used herein.

Pleuromutilins are among the most modern and most effective antibiotics currently available to veterinary medicine. Their most well-known representatives include Tiamutin® (active substance: tiamulin), which is described hereinbelow, and the more recent Econor® (active substance: valnemulin). Both substances can be very successfully used against a whole range of infectious bacterial diseases of the respiratory organs and of the digestive tract in animals and exhibit their full action even in those problem cases in which conventional antibiotics can, at best, be used only in the form of high-dose cocktails of a number of active substances, because of the resistance that is now occurring.

The spectrum of activity of the pleuromutilins includes, for example, pathogens such as *Streptococcus aronson, Staphylococcus aureus, Mycoplasma arthritidis, Mycoplasma bovigenitalium, Mycoplasma bovimastitidis, Mycoplasma bovirhinis, Mycoplasma sp., Mycoplasma canis, Mycoplasma felis, Mycoplasma fermentans, Mycoplasma gallinarum, Mycoplasma gallisepticum, A. granularum, Mycoplasma hominis, Mycoplasma hyorhinis, Actinobacillus laidlawii, Mycoplasma meleagridis, Mycoplasma neurolyticum, Mycoplasma pneumonia* and *Mycoplasma hyopneumoniae*.

In addition, WO 98/01127 describes, for valnemulin, outstanding activity against a disease complex that can occur wherever animals are held, for example for the purpose of transportation, in a very confined space (increased stocking density) and, as a result, are subjected to a high degree of stress. The most common pathogens that play a decisive role therein are *Mycoplasma hyopneumoniae, Serpulina* (formerly *Treponema*) *hyodysenteriae, Serpulina pilosicoli, Lawsonia intracellularis, Mycoplasma gallisepticum, Pasteurella multocida, Actinobacillus (Haemophilus) pleuropneumoniae* and *Haemophilus parasuis*, with diseases of the respiratory tract and other infections often occurring side by side and resulting in a complex clinical picture. All herd animals such as, for example, cattle, sheep and pigs, but also poultry are affected.

In today's large-scale farming of livestock, for example of pigs, cattle, horses, sheep and poultry, it is not possible, in the case of the animal diseases mentioned, to dispense with the administration of antibiotics because otherwise the diseases will rapidly spread through the entire stock of animals and, unless treated, will result in unsustainable losses. There is accordingly a great demand for effective antibiotics by means of which it is possible to gain control of infectious diseases in animals quickly before large numbers of the herd are affected.

Although, as antibiotics, pleuromutilins meet all expectations in terms of efficacy, they do have in common a drawback that cannot be underestimated, namely their relative instability in forms of administration which, by virtue of their being easy to handle, are of particular importance in veterinary medicine. As discussed in WO 01/41758, pleuromutilins, especially in the form of the free base, are not especially stable, which has obviously resulted in their having been used as acid addition salts, preferably as hydrochlorides, usually in the form of injection solutions. The acid addition salts have a storage stability at room temperature of up to five years. Oral administration in the case of animals has been rather the exception hitherto and can be used to only a limited extent, even in the form of a feed additive.

Whereas in the case of humans antibiotics can be administered in a very great variety of forms of administration, such as tablets, sugar-coated tablets, emulsions, injection solutions and the like, because it is possible to rely on the discipline of the human patient and his or her desire to recover, in the case of animals one is rapidly faced with considerable practical problems.

In animals, there must be a natural preparedness to take a medicinal preparation orally. Of course, it is possible to treat a single animal or a small number of animals forcibly and to administer an antibiotic in such a way that that the animal has to swallow it, or it is injected. Such forcible methods are, however, not acceptable for large stocks of animals because they are labour-intensive, require the veterinarian to be present in each individual case and, ultimately, result in high costs which cannot be passed on to the consumer of meat or dairy products because of the competitive situation that exists. In large-scale livestock farming, therefore, simple and reliable forms of administration are sought which the keeper of the animals can as far as possible put into practice independently or even fully automatedly and which keep the costs within acceptable limits.

A method that addresses those factors is the administration of precise doses of antibiotics incorporated in dry animal feed, that is to say in so-called feed pellets.

Nowadays, domestic animals and productive livestock such as, for example, pigs, but also cattle, sheep and poultry are frequently kept in animal buildings that are equipped with the most modern, fully automated feeding systems. In such cases, the feed is apportioned fully automatically according to the age and weight of the animal and transported to each animal and filled into its feeding trough at precisely determined times of day and in precisely determined daily amounts. The said feed pellets are frequently used in such fully automated systems. The pellets are a vegetable- and/or animal-based, compacted, highly compressed, concentrated dry feed, which may be enriched with additives such as proteins, vitamins and minerals. Such feed pellets are simply synthetic, pourable, round or elongate granules, spherules or, in dependence upon the production method, rod-shaped formed pieces of a uniform size matched to the breed and age of the animals and ranging from a few millimeters for poultry to about one centimeter for fully grown pigs and cattle. Commercial feed mills produce feed pellets by grinding the organic starting material, mixing the components in the desired composition and finally compressing them into pellets; the pellets are filled into sacks and delivered to the keeper of the animals, who fills them into the distribution system. A significant advantage of such pellets is their ease of handling, as a result of their uniformity, pourability and storage stability. They can readily be fully automatically emptied out of containers, measured into portions, transported via conveyor belts or pipes and given to each animal in a portion of precisely the correct amount. Pellets moreover take up much less space than fresh feed and, above all, are eaten by the animals willingly and without any problems.

It is accordingly advantageous to add to those pellets not only proteins and other nutrients such as vitamins and minerals but also, where required, antibiotics. This is already being carried out in practice but, in the case of the pleuromutilin class of active ingredients under discussion herein, one is faced with the particular difficulties described, which are specific to that substance class and will be explained in further detail hereinbelow.

It has been found that pleuromutilins are somewhat unstable, above all when in contact with feed material, especially vegetable and animal fibres, during the preparation of feed pellets, resulting in considerable losses as early as during the preparation process. In the preparation of feed pellets, the dried organic starting material of animal or vegetable origin is ground, is intimately mixed with the additives, vitamins, trace elements, antibiotics—in this case the pleuromutilin derivative—etc., that is to say is substantially homogenised, and then is moistened with about 5 to 10% by weight of water or steam and is compressed into pellets at elevated temperatures of about from 60 to 80° C., preferably from 65 to 75° C., under pressures of about from 1 to 100 kbar, usually from 25 to 100 kbar. Permanent higher temperatures, for example 100° C., tend to be disadvantageous and dramatically reduce the viscosity of the pellets. Short-term local temperature peaks inside the press, so-called flashes, of up to 200° C. are, in contrast, unproblematic. The dwell time of the mass in the press is about from 5 to 180 seconds, preferably from 10 to 90 seconds, and depends, inter alia, on the size of the pellets.

Whereas pleuromutilins in pure form withstand such temperatures per se very well and can be stored at room temperature for even a few months without any measurable loss of active ingredient, they decompose relatively rapidly under pressure and in intimate contact with animal or vegetable fibres in feedstuffs and under the prevailing elevated temperatures. It appears that contact with the fibres actually catalyses the decomposition process. Even when the elevated-pressure and elevated-temperature phase is kept as short as technically possible and the finished pellets are immediately cooled down to room temperature directly after the compression process, a quarter to a third of the active ingredient is nevertheless lost. Even though the degradation products do not have disadvantageous effects on the animals treated, the unavoidable loss of active ingredient inevitably results in a considerable increase in the cost of the final product.

It has, moreover, also been found that the pleuromutilin still intact in the pellets is much less storage-stable than, for example, the pure active ingredient. Even at room temperature, the degradation of the active ingredient continues in the finished pellets. After three months the active ingredient content has already dropped to less than 60%. That relative instability has also meant that, hitherto, the administration of an exact dose of active ingredient in the form of feed pellets could only be carried out for a period of about from 4 to 6 weeks after the pellets had been prepared. Accordingly, the keepers of the animals have hitherto been obliged to use only relatively freshly prepared pellets. They have been unable to store reasonable stocks of pellets long-term and have had to issue the feed mills with a new production order about every four to six weeks in order to be supplied with fresh feed having a guaranteed antibiotic content. Although that is technically feasible, it involves a high degree of logistical planning and has resulted in the feed mills repeatedly having to fulfil small orders which do not necessarily suit their production schedule, resulting in inconvenient waiting times and, especially, in an additional increase in the cost of the pellets.

For the reasons mentioned, therefore, much effort has been directed at stabilising pleuromutilins so that they withstand the elevated temperatures and pressures during pellet preparation without loss of active substance and also, when in the form of the finished pellets, have a long-term storage stability suitable for practical purposes.

Unsuccessful attempts at such stabilisation include, for example, (1) reduction of the active ingredient surface area by means of compression into granules, a very great variety of granule sizes having been tried; (2) sealing of the said active ingredient granules in a very great variety of protective layers, for example gelatin or various sugars and coatings; (3) enclosure of the active ingredient within porous materials such as, for example, various celluloses, starches, silicic acids or zeolites, with or without additional protective layers; and (4) chemical modification of the basic macrocyclic structure of the active ingredient. Although in a few cases chemical modification has resulted in improved stability of the compound per se, it has simultaneously resulted in loss of activity.

However, none of those attempts has resulted in an appreciably smaller loss of active ingredient on compression into feed pellets or in measurably improved storage stability. However, success has now been achieved, surprisingly, in providing the user with the user-friendly method of administering feed pellets in a form that no longer exhibits the mentioned drawbacks for the active ingredient. It is now possible, astonishingly, so to stabilise the pleuromutilin that it not only withstands pellet preparation undamaged but also survives for a sufficiently long storage period.

Although the present invention is illustrated hereinbelow with reference to the specific example of valnemulin, it is demonstrably equally applicable to Tiamutin®/tiamulin and other pleuromutilin derivatives having the basic macrocyclic structure of formula I shown at the beginning.

Within the context of the present invention preference is given to pleuromutilins of formula I below wherein $R_1$ is ethyl or vinyl;

(A) there is a single bond between carbon atoms 1 and 2, and Ra and Rb are H, and T is one of the following groups a to i:

a) —CH$_2$—OH;

b)

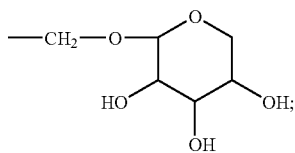

c) —(CH$_2$—X)$_m$—(CH$_2$)$_n$—N(R$_2$)(R$_3$) wherein X is —O—, —S—, —NH— or

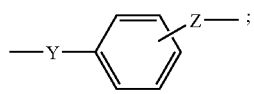

m is 0 or 1; n is an integer from 2 to 5; R$_2$ and R$_3$ are each independently of the other C$_{1-6}$alkyl or, together with the nitrogen atom to which they are bonded, form a 5- or 6-membered heterocycle containing as hetero moiety —S—, —O— or —N(R$_4$)— wherein R$_4$ is C$_{1-6}$alkyl or C$_{1-6}$hydroxyalkyl, and Y and Z are each independently of the other —O— or —S—;

d) —CH$_2$—S—(CH$_2$)$_k$—N(R$_5$)(R$_6$) wherein k is an integer from 2 to 5; and R$_5$ and R$_6$ are each independently of the other C$_{1-6}$alkyl;

e) —CH$_2$—S—C(CH$_3$)$_2$—CH$_2$—NH—C(O)—R$_7$ wherein R$_7$ is C$_{1-6}$alkyl substituted by —NH$_2$ or is a saturated five-membered heterocycle containing one or two hetero atoms selected from —S— and —NH—;

f) —CH$_2$—S—C(CH$_2$)$_l$—R$_8$ wherein l is 0 or 1 and R$_8$ is the group

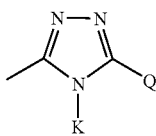

wherein K is H, C$_{1-6}$alkylsulfonyl, —NH$_2$, —CHO, —N(R$_9$)(R$_{10}$), —S—(CH$_2$)$_q$—N(R$_9$)(R$_{10}$) or —C(G)-NHR$_{11}$, G being oxygen or sulfur, R$_9$ and R$_{10}$ being each independently of the other H, C$_{1-6}$alkyl, C$_{1-6}$alkylsulfonyl; C$_{1-6}$hydroxyalkyl, C$_{1-6}$dihydroxyalkyl or unsubstituted or C$_{1-6}$alkylsulfonyl-substituted C$_{1-6}$alkanoyl; or R$_9$ and R$_{10}$, together with the nitrogen atom to which they are bonded, forming unsubstituted or substituted piperazinyl wherein the second nitrogen atom is substituted by a substituent from the group C$_{1-6}$alkyl, C$_{1-6}$hydroxyalkyl and C$_{1-6}$dihydroxyalkyl; R$_{11}$ being C$_{1-6}$alkyl or C$_{1-6}$alkylcarbonyl; Q is H, —NH$_2$, —CF$_3$, C$_{1-6}$alkyl, pyridyl or —N(R$_9$)(R$_{10}$), R$_9$ and R$_{10}$ being as defined above;

g) —CH$_3$, —CH$_2$Cl, CH$_2$Br, —CH$_2$SCN, —CH$_2$—NH$_2$, —CH$_2$—N$_3$, —CO—OH, —CH$_2$—OCOCH$_3$ or

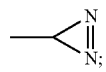

h) —N(R$_{15}$)(R$_{16}$) wherein R$_{15}$ and R$_{16}$ are the same or different and are selected from the group consisting of H, an unsubstituted or substituted, straight-chain or branched, saturated or unsaturated C$_{1-6}$hydrocarbon radical; an unsubstituted or substituted, saturated or unsaturated C$_{3-8}$cycloalkyl radical; an unsubstituted or substituted heterocycle; and an unsubstituted or substituted aryl radical; or R$_{15}$ and R$_{16}$, together with the nitrogen atom to which they are bonded, form a 3- to 8-membered ring not containing a further hetero atom or containing a further hetero atom from the series —N—, —O— and —S—; or R$_{15}$ is one of the groups mentioned and R$_{16}$ is —SO$_2$R$_{17}$, —C(O)R$_{18}$, —O—R$_{19}$ or N(R$_{19}$)(R$_{20}$); R$_{17}$ being selected from the group consisting of an unsubstituted or substituted, straight-chain or branched, saturated or unsaturated C$_{1-6}$hydrocarbon radical, an unsubstituted or substituted, saturated or unsaturated C$_{3-8}$cycloalkyl radical, an unsubstituted or substituted heterocycle, an unsubstituted or substituted aryl radical, an unsubstituted or substituted C$_{1-6}$alkylamino radical and an unsubstituted or substituted arylamino radical; R$_{18}$ being selected from the group consisting of H, an unsubstituted or substituted, straight-chain or branched, saturated or unsaturated C$_{1-6}$hydrocarbon radical, an unsubstituted or substituted, saturated or unsaturated C$_{3-8}$cycloalkyl radical, an unsubstituted or substituted heterocycle and an unsubstituted or substituted aryl radical; R$_{19}$ and R$_{20}$ being the same or different and being selected from the group consisting of an unsubstituted or substituted, straight-chain or branched, saturated or unsaturated C$_{1-6}$hydrocarbon radical, an unsubstituted or substituted, saturated or unsaturated C$_{3-8}$cycloalkyl radical, an unsubstituted or substituted heterocycle and an unsubstituted or substituted aryl radical or, together with the nitrogen atom to which they are bonded, forming a 3- to 8-membered cyclic group which may optionally contain a further hetero atom selected from the group consisting of —N—, —O— and —S—;

(B) there is a double bond between carbon atoms 1 and 2, and Ra and Rb are H, and T is the following group i:

i) —CH$_2$—CO—R$_{12}$ wherein R$_{12}$ is an unsubstituted or substituted, nitrogen-containing, 5- or 6-membered heterocycle, an unsubstituted or substituted aryl radical or the group —CH$_2$—R$_{13}$, R$_{13}$ is halogen or —SR$_{14}$, and R$_{14}$ is amino-C$_{1-6}$alkyl or an unsubstituted or substituted, nitrogen-containing, 5- or 6-membered heterocycle or an unsubstituted or substituted aryl radical, substituents for the said heterocycle or aryl radical being from one to three radicals selected from the group consisting of OH, CN, NO$_2$, N$_3$, C$_{1-6}$alkyl, C$_{1-6}$alkoxy, C$_{1-6}$-alkoxy-C$_{1-6}$alkyl, di-N—C$_{1-6}$alkylamino, C$_{1-6}$acylamino, C$_{1-6}$acylcarbonylamino, C$_{1-6}$-acyloxy, C$_{1-6}$carbamoyl, mono- and di-N—C$_{1-6}$alkylcarbamoyl, C$_{1-6}$acyloxycarbonyl, C$_{1-6}$alkylsulfonyl, C$_{1-6}$alkylsulfinyl and benzyl;

(C) there is a single bond between carbon atoms 1 and 2, and Ra is H, OH or F, and Rb is H; or Ra is H, and Rb is F; and T is the following group k:

k) —CH$_2$—CO—R$_{12}$ wherein R$_{12}$ is as defined for the group i;

including the physiologically tolerable acid addition salts and quaternary ammonium salts thereof.

The free compounds of formula I can be converted into their acid addition salts, and vice versa, by known methods.

Of the acid addition salts greatest preference is given to the HCl salt. The quaternary ammonium salts can likewise be prepared by methods known per se.

Unless otherwise defined, the substituent definitions are based on what will be generally understood by an average chemist. Within the context of formula I above, alkyl per se or as part of a substituent is, depending upon the number of carbon atoms, methyl, ethyl, n-propyl, isopropyl, n-butyl, sec-butyl, tert-butyl, isobutyl etc. "Halogen" is fluorine, chlorine, bromine or iodine; preferably fluorine, chlorine or bromine and especially chlorine.

The preferred saturated or unsaturated, 5- or 6-membered, heterocyclic rings include those that contain one or more hetero atoms, suitable hetero atoms being, especially, sulfur and nitrogen. An especially preferred sub-group of such heterocycles contains 1, 2 or 3 nitrogen atoms and no other hetero component. Of those, special emphasis is to be given to those unsaturated, 5- or 6-membered, heterocyclic rings that contain a single nitrogen atom as the hetero component, for example pyridine, pyrrole and 5,6-dihydro-3H-pyrrole. Suitable unsaturated, 5- or 6-membered heterocyclic rings containing two nitrogen atoms are, for example, imidazole, pyridazine and pyrimidine. Such rings may also have one or more fused-on phenyl rings. Typical examples are benzimidazole, quinoline, isoquinoline and phthalazine. Suitable 5- or 6-membered heterocyclic rings containing three nitrogen atoms are, for example, 1,2,4-triazoles. Another group of preferred heterocycles contains one nitrogen atom and one sulfur atom. Those include, for example, the various thiazoles, 4,5-dihydrothiazole and benzothiazole. A typical example of a heterocycle containing two nitrogen atoms and one sulfur atom is 1,3,4-thiadiazole. Aryl or an aryl radical is, especially, phenyl or naphthyl, which, unless specifically defined, may be unsubstituted or may carry up to four identical or different substituents selected from the group consisting of OH, nitro, amino, cyano, halogen, $C_{1-6}$alkyl, $C_{1-6}$alkoxy, $C_{1-6}$alkoxy-$C_{1-6}$alkyl, halo-$C_1$-alkyl, mono-N—$C_{1-6}$alkylamino, di-N—$C_{1-6}$alkylamino, $C_{1-6}$acyloxy, $C_{1-6}$acylamino, $C_{1-6}$acylcarbonylamino, $C_{1-6}$carbamoyl, mono- and di-N—$C_{1-6}$alkylcarbamoyl, $C_{1-6}$acyloxycarbonyl, $C_{1-6}$alkylsulfonyl, $C_{1-6}$alkylsulfinyl and benzyl. Unless specifically defined, suitable substituents are the same as for heterocyclic rings, the heterocycles likewise being substituted one or more times by identical or different radicals. Heterocycles to which special emphasis is to be given are: 3-pyridyl, 4-pyridyl, pyrimidin-2-yl, 1,3,4-thiazol-2-yl, benzothiazol-2-yl, 2H-1,2,4-triazol-3-yl, azabicycloheptyl, azabicyclooctyl and piperidyl.

The present invention relates especially to compounds of formula I wherein $R_1$ is vinyl, there is a single bond between carbon atoms 1 and 2, and Ra and Rb are hydrogen or halogen, preferably hydrogen, and T is as defined for formula I; including the physiologically tolerable acid addition salts and quaternary ammonium salts thereof.

Special preference is given to pleuromutilin derivatives of formula I wherein
$R_1$ is vinyl; there is a single bond between carbon atoms 1 and 2;
Ra and Rb are H, and
T is —$CH_2$—S—$(CH_2)_k$—N($R_5$)($R_6$) wherein k is an integer from 2 to 5; and $R_5$ and $R_6$ are each independently of the other $C_{1-6}$alkyl; including the physiologically tolerable acid addition salts and quaternary ammonium salts thereof. Within that group, very special preference is given to the pleuromutilin derivative wherein T is —$CH_2$—S—$(CH_2)_2$—N($C_2H_5$)($C_2H_5$).

Preference is likewise given to pleuromutilin derivatives of formula I wherein
$R_1$ is vinyl; there is a single bond between carbon atoms 1 and 2;
Ra and Rb are H, and T is —$CH_2$—S—$C(CH_3)_2$—$CH_2$—NH—C(O)—$R_7$ wherein $R_7$ is $C_{1-6}$alkyl substituted by —$NH_2$ or a saturated five-membered heterocycle containing one or two hetero atoms selected from —S— and —NH—; including the physiologically tolerable acid addition salts and quaternary ammonium salts thereof. Within that group, preference is given to the pleuromutilin derivatives of formula I wherein T is —$CH_2$—S—$C(CH_3)_2$—$CH_2$—NH—C(O)—$R_7$ wherein $R_7$ is $C_{1-6}$alkyl substituted by —$NH_2$ and especially the pleuromutilin derivative wherein T is —$CH_2$—S—$C(CH_3)_2$—$CH_2$—NH—C(O)—CH($NH_2$)—CH($CH_3$)$_2$.

Within the context of the present invention, very special preference is accordingly given to the compounds tiamulin and valnemulin, especially valnemulin by virtue of its broad-spectrum activity. As already mentioned, both substances are commercially available. The chemical structure of those two preferred substances is as follows:

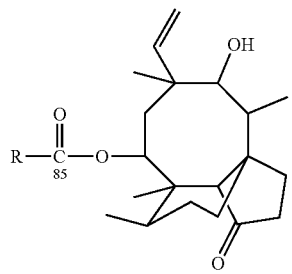

Tiamutin ® / tiamulin      Econor ® / valnemulin

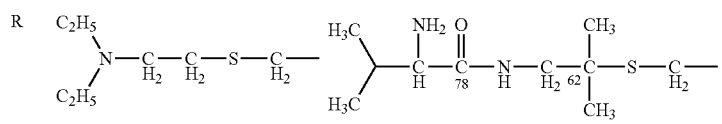

Compounds of formula I are described in detail in the literature, for example in the references given below:

The compound of formula I wherein $R_1$ and A are as defined for formula I and T is as defined for group a has been isolated by Kavanagh et al. and described in Proc. Natl. Acad. Soc. 37, 570-574 (1951). That compound is the basic representative of the class of substances discussed herein, namely pleuromutilin. In U.S. Pat. No. 4,247,542, it is indicated that the structure of pleuromutilin was later found to be characterised in that Y in formula I above is —$CH_2$—OH. The same US patent also describes a compound of formula I wherein $R_1$ is in turn vinyl, there is a single bond between carbon atoms 1 and 2, and Ra and Rb are H, and T is —$CH_2$-β,D-xylopyranosyl.

The compound of formula I wherein $R_1$ and A are as defined for formula I and T is as defined for group b is described in U.S. Pat. No. 4,129,721.

Compounds of formula I wherein $R_1$ and A are as defined for formula I and T is as defined for group c are described in U.S. Pat. No. 4,148,890.

Compounds of formula I wherein $R_1$ and A are as defined for formula I and T is as defined for group d are described in U.S. Pat. No. 3,919,290, including the substance already specifically mentioned several times, tiamulin, which is available under the trade-name Tiamutin®. Compounds of formula I wherein $R_1$ and A are as defined for formula I and T is as defined for group e are described in EP-0 153 277, including valnemulin, which has already been mentioned several times and which is also known from WO 98/01127.

Compounds of formula I wherein $R_1$ and A are as defined for formula I and T is as defined for group f are described in U.S. Pat. No. 4,428,953.

Compounds of formula I wherein $R_1$ and A are as defined for formula I and T is as defined for group g are described in U.S. Pat. No. 3,979,423.

Compounds of formula I wherein $R_1$ and A are as defined for formula I and T is as defined for group h are described in WO 97/25309.

Compounds of formula I wherein $R_1$ and B are as defined for formula I and T is as defined for group i are described in WO 01/14310.

Compounds of formula I wherein $R_1$ and C are as defined for formula I and T is as defined for group k are described in WO 01/14310.

It will be understood that the individual examples specifically mentioned in those references are included in the preferred embodiments of the present invention.

The literature discloses a series of tests involving the addition of medicaments, including tiamulin, to animal feed but those tests are unable to solve the technical problem underlying the present invention. Some of those references will be discussed briefly below:

EP 0 165 577 relates to the provision of a feedstuff additive comprising zinc bacitracin which, after mixing with feed or when pelletised, has improved stability and makes prolonged storage possible. The improved stability is achieved by providing the feedstuff additive comprising zinc bacitracin with a polymeric coating, with polymers such as polysaccharides, polyacrylates, fats, fat-like compounds or waxes being used as coating.

The Derwent Publication XP002197610 [JP 03 101619 A SDS BIOTECH CORP] of 26.04.1991 relates to a non-bitter veterinary medicament in granule form consisting of a zeolite carrier material and tiamulin.

The Derwent Publication XP002198060 [JP 63 033330 A NIPPON KAYAKU KK] of 13.02.1988 relates to an oral antibacterial administration form of, inter alia, tiamulin based on sodium polyacrylate, resulting in improved absorption of the active ingredient. The administration form consists of a powder, which may also be compressed into granules or tablets and mixed in with animal feed.

EP-0 707 798 describes a method of preparing feeds that comprise pharmacologically active substances. The method is especially characterised in that the pharmacologically active substances are applied individually or in admixture in a suitable galenical gel-form preparation, in the form of a sprayable gel, to a physically prepared feedstuff.

European Patent Application EP-0 658 313 describes granules consisting of a core and a coating. The core consists of organic, especially vegetable, or inorganic material and has a diameter of from 100 to 800μ. The coating consists of water-soluble polymers comprising the active ingredient, which polymers dissolve in an aqueous medium and, especially, in gastric juice. The active ingredient is incorporated in that coating or adheres thereto. During production, the core is prepared first. The surface of the core is treated with acid and is then sprayed with an aqueous solution of the active ingredient. The aim is to prepare fine granules that can be mixed in with the animal feed without any difficulty. In contrast to the present invention, the granules described in that reference do not result in any significant stabilisation of the active ingredient and are therefore not suitable for the provision of animal feed pellets comprising a pleuromutilin derivative. The active ingredient is, also in contrast to the present invention, released in the stomach.

It has now been found, surprisingly, that the pleuromutilin derivative can be enclosed in microspherules by methods known per se; those microspherules can be introduced into the dry animal feed and compressed into feed pellets at elevated pressure and at elevated temperature and subsequently dried, without the hitherto unavoidable loss of active substance. This newly obtained stability of the active substance in the pellets results, moreover, in extremely high storage stability for the finished feed. At room temperature, such feed pellets can now be stored stably for many months, that is to say the active ingredient content remains virtually constant.

The active substance enclosed in the microspherules not only results in the said unforeseen improvement in stability but also, quite independently, has the further advantage that, in contrast to the pure active substance, the microspherules are not subject to dust formation, do not form lumps, are outstandingly pourable and shield the active substance from undesired influences from the outside. For example, unintentional inhalation or contact with the skin and eyes are, as a result, avoided during handling. Having been embedded in the microspherules, the active substance, which is in any case not approved for use in humans, can be handled simply and safely without special protective measures having to be taken. Because the microspherules exhibit virtually no adhesion to apparatus surfaces and neither form lumps or crusts nor stick together in any other way, the apparatus used, for example in the feed mills, can be cleaned with little technical difficulty; simple vacuum-removal is often quite sufficient.

The use of these microspherules moreover results in a further advantage in use. When antibiotics are administered orally, a loss of appetite which increases in the course of the therapy is observed in sensitive human patients. Depending upon the severity of the case, the physician will then change over to another form of administration, for example to injection or to suppositories, in order to by-pass the stomach. In animals, the same effect is observed in individual cases. The loss of appetite is reflected in the refusal to eat a sufficient amount of feed. Also, the feed is less well metabolised and the desired increase in weight does not occur. Because such animals eat less feed, the oral therapy is also jeopardised. Changing-over to suppositories is not an option in the case of animals, and injections have the disadvantages already described, the elimination of which is an aim of the present invention. When the microspherules according to the invention are used orally, the said over-sensitivity and associated refusal of feed are not observed, which is presumed to be related to the fact that the matrix of the microspherules is acid-resistant.

Bioavailability studies indicate that the microspherules pass through the stomach in an intact state and release the active ingredient only in the alkaline medium of the intestine. When comparative feed tests are carried out on piglets using a) feed pellets that comprise free valnemulin hydrochloride or commercially available ECONOR® and b) feed pellets prepared according to Example 2 that comprise the valnemulin hydrochloride enclosed in microspherules, with blood samples being taken from the test animals hourly and the valnemulin concentration present in the blood plasma being measured, it is found that in case a) the concentration of active ingredient rises rapidly before reaching its maximum value after 2-3 hour. After 8-10 hours, the curve then falls off again and approaches zero. In case b), with the microspherules, the increase in active ingredient concentration begins after a delay of about 1-2 hours, reaches its maximum value after about 3-4 hours and, after about 10-12 hours, falls towards zero. Consequently, although in case b) there is a slight delay in establishing effective blood level values, that does not have an adverse effect on the therapy. This new method makes available a form of administration that is gentle on the stomach and that makes oral therapy even more efficient.

If desired, by means of additives such as, for example, sodium hydrogen carbonate, the microspherules according to the invention can be made to dissolve, and release the active ingredient, as early as in the acid medium of the stomach. In many cases, however, that is not desired.

In the context of the present invention, microspherules (or "microspheres") are understood to be microscopically small, mostly spherical polymeric matrix particles having an average size of about from 1 μm to about 5000 μm, usually from 50 μm to 3000 μm. The pleuromutilin derivative is embedded therein. They are accordingly extremely small spheres comprising a compact polymeric matrix in which the active ingredient, in solid or liquid form, is highly dispersed, not merely coated. It could be described as a special case of encapsulation.

The method used in the present invention for preparation of the microspherules is known per se; likewise the materials used for the encapsulation and the pleuromutilin derivatives employed. However, the microspherules prepared for the first time in that manner and the feed pellets comprising those microspherules and the oral use thereof in combating infectious diseases in animals are new.

The microspherules can be prepared analogously to the methods described in the references mentioned below:
Shigeru Goto et al., Journal of Microencapsulation, 1986, Vol. 3, No. 4, 293-305;
Shigeru Goto et al., Journal of Microencapsulation, 1986, Vol. 3, No. 4, 305-316 or
U.S. Pat. No. 3,714,065 (corresponds to DE-2 105 039).

The main focus of the present invention is less on the aspects of the preparation of microspherules or the oral use of pleuromutilins than on the provision of novel feed pellets that comprise pleuromutilin derivatives stabilised in the form of microspherules and that, as a result, undergo no significant loss of active ingredient either during preparation or during storage. The invention consists in implementing stabilisation of the active substance in feed pellets. This invention is intended to assist the practitioner in solving existing technical problems and to provide him with means by which he can store feed pellets comprising pleuromutilins for relatively long periods of time and administer them to domestic animals and productive livestock without a large outlay in terms of personnel, time and logistics. In the final analysis, not only does that save time and money but also quite significantly increases the safety and reliability in practical use.

The microspherules are advantageously prepared in a two-phase system consisting of a first, organic or organic-aqueous, phase and a second, oily phase. The organic or organic-aqueous phase consists of a solution or dispersion of the polymeric components suitable for the formation of microspherules, solvent and the pleuromutilin derivative to be enveloped. The oily phase is a dispersion of aluminium mono-, di- or tri-stearate, sodium stearate, calcium stearate or magnesium stearate in a suitable oil, most advantageously liquid paraffin or silicone oil. Other, for example non-ionic, emulsifiers or dispersants such as sorbitan mono-oleate (Span-80®) may, however, also be used. The volume of the oily phase advantageously exceeds the volume of the organic phase several times. The two phases are intimately mixed together with vigorous stirring or are even homogenised under high pressure or with the aid of a static mixer. Microscopically small polymeric particles are formed in the process. The microspherules comprise the active ingredient in highly dispersed form and are not soluble in the reaction mixture so that they can be separated off by decanting or filtering, washed and dried.

The stirring of the two phases is also important for the formation of the microspherules. In general there is used a stirring apparatus having a propeller-shaped stirrer at relatively speeds of rotation of at least 100 rpm to about 1500 rpm, ensuring vigorous intermixing of the two phases and rapid formation of microspherules. A static mixer may, of course, also be used.

In detail, preparation of the microspherules is carried out in the following steps:
(a) preparation of a solution of a polymer suitable for the formation of the matrix for the microspherules, which polymer is selected from the group consisting of shellac and a polymer based on cellulose, acrylic acid or methacrylic acid, maleic anhydride, polyvinylpyrrolidone or polyvinyl alcohol, by dissolving the shellac or the polymer in an organic solvent having low affinity for paraffin oil or silicone oil and a dielectric constant of from about 10 to about 40, where appropriate with the addition of water;
(b) introduction of the pleuromutilin derivative into that shellac or polymer solution, with stirring, so that a first, organic phase, which is not miscible with paraffin oil or silicone oil, is formed;
(c) introduction of that first phase, with vigorous stirring, for example using a static mixer or a high-pressure homogeniser, into the second, oily phase consisting of paraffin oil or silicone oil, and continued stirring of the resulting mixture until the microspherules comprising the pleuromutilin derivative are formed on evaporation or removal of the solvent;
(d) isolation, and, where appropriate, washing and drying, of the microspherules.

Shellac is sufficiently known in the pharmaceutical industry, for the preparation of neutral-tasting sugar-coated tablet coatings.

Suitable starting materials for cellulose-based polymers are, for example, cellulose acetate phthalate or cellulose acetate N,N-di-n-butylhydroxypropyl ether.

Starting materials that can be used for acrylic acid- or methacrylic acid-based polymers are, for example, methacrylate/methacrylic acid copolymer, 2-methyl-5-vinyl-pyridine/methacrylate/methacrylic acid copolymer, methyl methacrylate/methacrylic acid copolymer, methyl methacrylate/methacrylic acid copolymer, methyl methacrylate/maleic anhydride copolymer or methyl methacrylate/maleic anhydride copolymer.

Suitable starting materials for maleic anhydride-based polymers are, for example, vinyl methyl ether/maleic anhydride copolymer or styrene/maleic anhydride copolymer. Within the context of the present invention, special preference is given to acrylic acid- or methacrylic acid-based polymers as envelope for the microspherules. Most advantageously, commercially available products are used for their preparation. Such products are polymerisation products of acrylic acid and acrylic acid esters having a low content of quaternary ammonium groups. Commercial products such as Eudragit® E, L or S from Röhm, Darmstadt, Germany are very suitable. Eudragit® E is a cationic polymer of dimethylaminoethyl methacrylate and a neutral methacrylic acid ester. Eudragit® L and S are anionic copolymers of methacrylic acid and methacrylic acid methyl ester.

Suitable starting materials for polyvinylpyrrolidone-based polymers are, for example, polyvinylpyrrolidone.

Suitable starting materials for polyvinyl alcohol-based polymers are, for example, polyvinyl alcohol itself.

The oily phase is used in relatively large amounts so that the volume ratio of organic to oily phase is about in the range from 1:20 to 5:10.

Normally, the procedure is carried out at room temperature or at slightly elevated temperature, that is to say in a temperature range of from about 20° to 45° C. Room temperature is, however, entirely sufficient.

Suitable organic solvents for the first, organic phase are, for example, solvents that mix with the oily phase as little as possible and that are readily volatile. Those that have a dielectric constant of from 10 to 40 are very suitable. A number of such solvents are shown by way of example in the following Table.

| Solvent | Dielectric constant | Solvent | Dielectric constant |
|---|---|---|---|
| methanol | 32.6 | phenol | 9.8 |
| ethanol | 24.3 | acetone | 20.7 |
| isopropanol | 18.7 | acetic acid | 9.7 |
| butanol | 17.1 | acetic anhydride | 20.7 |
| benzyl alcohol | 13.1 | nitromethane | 35.9 |
| ethylene glycol | 37.7 | ethylenediamine | 14.2 |
| propylene glycol | 35.0 | Cellosolve acetic acid | 16 |

The pure solvents or mixtures of such solvents may be used, for example an acetone-ethanol mixture (1:1). Very good results are achieved by adding a small amount of water, that is to say about from 1 to 5 parts of water by volume to from 10 to 50 parts of organic solvent by volume. Preference is given to acetone-water mixtures (about 30:1).

It has proved advantageous to add to the second, oily phase, before it is used, aluminium mono-, di- or, preferably, tristearate, sodium stearate, calcium stearate, magnesium stearate or another, for example non-ionic emulsifier or dispersant, such as sorbitan mono-oleate (Span-80®), with vigorous stirring so that a homogeneous dispersion is formed. Such addition promotes especially rapid formation of microspherules of a very uniform size. As a result, the microspherules being formed are prevented from coalescing with one another during preparation. When the first phase comprising the polymer and the pleuromutilin derivative consists of an acetone-water mixture and the two phases are combined with stirring at from 800 to 1000 rpm, then microspherules having a uniform size of from 50 to 1000 μm are obtained. The pleuromutilin and stearate are advantageously used in a weight ratio of from 0.5:1 to 10:1, preferably about 1:1.

The microspherules may be washed, for example with diethyl ether, light petroleum or n-hexane, methylcyclopentane or, preferably, cyclohexane. The solvent is most gently removed at room temperature in vacuo. It is self-evident that the solvent is so removed that residues are as low as possible.

The microspherules obtained by the above method have a relatively hard polymeric envelope. In order to achieve greater ductility, about from 3 to 10% of a plasticiser by weight, based on the polymer, may be added to the organic phase. Suitable plasticisers are triacetin; acetylated monoglycerides; glycerol; polyethylene glycol, for example PEG 400 or PEG 600; phthalates, such as diethyl phthalate or dibutyl phthalate; citrates, such as triethyl citrate, acetyl triethyl citrate, tributyl citrate or acetyl tributyl citrate; and vegetable oils, such as castor oil, rapeseed oil or sunflower oil. An addition of about from 4 to 10% of triethyl citrate is feasible. In general, however, the addition of plasticisers is not necessarily desirable because it has been found that the higher the proportion of plasticiser the lower the storage stability of the finished feed pellets. The addition of plasticisers accordingly tends to act counter to the desired improvement in stability, which does not mean, however, that it is not possible to add plasticiser, especially in relatively small amounts. Plasticisers lower the glass transition temperature. The active ingredient is, in our experience, no longer protected during preparation of the feed pellets when the glass transition temperature is lower than about 100-150° C.

Feed pellets are usually produced by feed mills. Ground cereal is generally used as base. To that base there are added further constituents such as oil and vegetable and animal proteins. All the constituents are intimately mixed together in a grinding or mixing apparatus, sprayed with water or treated with steam and, at elevated temperature, extruded, i.e. pressed, through a round nozzle having a diameter of about from 2 to 15 mm. During that pressing process, the moistened material is compacted and it leaves the nozzle in the form of a relatively hard bar, which at the nozzle outlet is cut into pieces of desired length, for example about from 5 to 25 mm in length, using a cutting apparatus. The resulting pellets, which are still warm, dry in the air as they are transported away or are taken on a conveyor belt through a heating chamber and dried at about from 80 to 120° C. The finished pellets are rod-shaped or cylindrical; they have a relatively smooth surface and are readily pourable without crumbling or forming dust. They generally have a density of about 1.2 g/cm$^3$.

In general, the procedure for preparation of the stabilised feed pellets according to the invention is exactly as for preparation of normal feed pellets without added medicament. However, before the pressing process the microspherules and the organic, ground and homogenised feed constituents are intimately mixed together, moistened with about from 5 to 10% by weight of water or steam and compressed into feed pellets at elevated temperatures of about from 60 to 80° C., preferably from 65 to 75° C. Good homogenisation is most advantageously achieved when the microspherules are first intimately mixed together with a relatively small portion of the rest of the feed components, as a result of which a so-called premix having a relatively high proportion of microspherules is obtained. A portion of that premix is then mixed together with further feed material to form a further partial mix and that partial mix is, in a final step, diluted to the final concentration with additional feed material. That dilution results in an especially uniform distribution of the encapsulated active ingredient in the pellets.

The pellets are allowed to cool to room temperature and are packed in paper sacks or other suitable containers for storage or for transportation to the end consumer. No special precautionary measures are necessary because the pellets are extremely storage-stable and comprise the active ingredient in a coated foam which shields the active ingredient from environmental influences. No active ingredient comes through to the outside from these storable pellets.

Measurement of the amount of active ingredient before and after compression into pellets shows, surprisingly, that the pelletisation using microspherules does not result in any measurable loss of active ingredient.

IMPLEMENTATION EXAMPLES

Example 1

Preparation of Valnemulin HCl Microspherules Enveloped with Methacrylic Resin

| Composition | Weight |
|---|---|
| valnemulin HCl (active substance) | 12.5 g |
| excipients | |
| Eudragit ® L 100* | 37.5 g |
| aluminium monostearate | 11.25 g |
| water | 9.4 g |
| acetone | 303.1 ml |
| light liquid paraffin | 1250 ml |
| total weight | 1351.94 g |

*Eudragit ® is a commercial product of Röhm. It consists of the components methacrylic acid butyl ester, (2-dimethylaminoethyl) methacrylate and methyl methacrylate copolymer.

Step 1: The Eudragit is dispersed in 100 ml of acetone at room temperature in a glass beaker with stirring (800 rpm/5 minutes/magnetic stirrer). Stirring of the dispersion is continued under the same conditions and water is added. After 10 minutes, the polymer has dissolved completely. Whilst continuing to stir, the active substance, in this instance valnemulin, is added in portions. After a further 10 minutes, a clear solution is obtained.

Step 2: In a 2-liter reactor provided with a 3-blade propeller stirrer (1000 rpm), aluminium monostearate is dispersed in light liquid paraffin at room temperature. After 10 minutes, the dispersion is homogeneous.

Step 3: The solution obtained in Step 1 is added to the dispersion obtained according to Step 2 at room temperature, whilst continuing to stir (1000 rpm). An emulsion is formed, which is further stirred at 800 rpm for 24 hours at room temperature. (Alternatively, the emulsion may also be heated first to 40° C. over the course of 1 hour under pressure (200 mbar) and the pressure and temperature maintained for a further 2 hours.) In both cases, microspherules (microspheres), that is to say microcapsules consisting of methacrylic resin, in which the active substance is enclosed, are formed.

Step 4: After switching off the stirrer, the microspherules sink to the bottom of the reactor, and the supernatant paraffin and aluminium monostearate are decanted off as completely as possible. The microspherules are washed several times with cyclohexane (three times/Buchner funnel/fabric filter) and excess cyclohexane is removed in vacuo.

Example 2

Preparation of Feed Pellets for Pig Breeding: (Piglet Feed)

80 g of the active substance (valnemulin) are added to 3920 g of conventional, ground and homogenised, dry piglet feed and intimately mixed using a spiral mixer. By that means, 4000 g of premix are obtained. The 4000 g of premix are added to a further 36 kg of conventional, ground and homogenised, dry piglet feed in a 100-liter spiral mixer and likewise intimately mixed. The resulting 40 kg of partial mix are then mixed into a further 360 kg of conventional, ground and homogenised, dry piglet feed, transferred to an extruder and compressed into rod-shaped feed pellets of about 10 mm in length and about 6 mm in width at 68-72° C. and at a pressure of 10-100 kbar. During the compression process, steam (2 bar, 136° C.) is used. The dwell time in the heated portion of the extruder is set at about 75 seconds. The finished pellets are filled into sacks of 25 kg each.

Example 3

Stability Testing of Feed Mixtures Comprising Either the Free Active Ingredient, Commercially Available Coated Active Ingredient or Active Ingredient Embedded in Microspherules In accordance with Preparation Example 2, three types of piglet feed pellets A, B and C are prepared using differently pre-treated active ingredient, but identical amounts of active ingredient. Pellets of Type A comprise commercially available ECONOR® 50% (active ingredient valnemulin), in which the active ingredient is coated with hydroxypropyl methylcellulose (HPMC). Pellets of Type B comprise the pure active ingredient valnemulin in the form of the hydrochloride and pellets of Type C comprise the microspherules prepared in accordance with Preparation Example 1 comprising embedded valnemulin hydrochloride.

For measurement of the stability, the three types of feed pellets are prepared in accordance with Preparation Example 2 and the first samples of 50 g each are taken immediately after preparation. 9 samples of Type A are taken, 9 samples of Type B are taken and, for Type C, three different batches of feed pellets are prepared, which differ from one another slightly in the composition of the feed material. 9 samples are likewise taken from each of those batches. All the samples are immediately tested and the content of intact valnemulin in each sample is analytically determined. The remaining feed pellets are divided into two equal portions and transferred to two climate chambers for the actual long-term studies. Chamber (I) is at 25° C. and a relative humidity of 60%, simulating normal storage at room temperature. Chamber (II) is at an elevated temperature of 40° C. and an elevated relative humidity of 75%, simulating an extended storage period.

At one-month intervals, 3 samples of 50 g each are taken from each chamber and from each type and batch of feed pellets and the intact valnemulin content is determined.

The average values and the associated standard deviation are listed in Tables 1 and 2 below for the differing climate conditions.

TABLE 1

25° C./relative humidity of 60%
Data in [% valnemulin/(standard deviation)]

| | immediately after pelletisation | after 1 month | after 2 months | after 6 months |
|---|---|---|---|---|
| Type A ECONOR ® 50%, HPMC | 98.36%/ (9.28) | 76.68%/ (2.56) | 70.54%/ (1.38) | 37.31%/ (1.39) |
| Type B valnemulin HCl | 78.38%/ (8.66) | 43.55%/ (15.37) | 47.30%/ (1.00) | 26.62%/ (0.87) |
| Type C valnemulin in microspherules | 102.93%/ (6.49) | 99.69%/ (3.18) | 99.20/ (2.11) | 96.22%/ (3.91) |

TABLE 2

40° C./relative humidity of 75%
Data in [% valnemulin/(standard deviation)]

| | immediately after pelletisation | after 1 month | after 2 months | after 6 months |
|---|---|---|---|---|
| Type A ECONOR ® 50%, HPMC | 98.36%/ (9.28) | 38.72%/ (2.28) | 25.35%/ (1.13) | 6.83%/ (0.96) |
| Type B valnemulin HCl | 76.38%/ (8.66) | 34.65%/ (15.98) | 15.33% (0.24) | 9.14%/ (0.90) |
| Type C valnemulin in microspherules | 102.93% (6.49) | 96.42%/ (1.74) | 89.12%/ (3.19) | 79.70%/ (6.62) |

The Tables show quite clearly that the valnemulin present in feed pellets of Types A, B and C is of varying stability. Pure valnemulin (Type B) is obviously degraded the fastest and already undergoes a loss of about 21% during pelletisation. After two months at normal room temperature, the valnemulin content in Type B drops to less than 50% and, in the case of elevated temperature at 40° C., even drops to less than 20%. In the case of valnemulin coated with HPMC in Type A, the degradation of valnemulin is indeed somewhat less, but is still considerable. The active ingredient loss of about 1% during pelletisation may be disregarded but, after 2 months, storage at 25° results in a significant loss of about 30% and, at 40° C., even about 76%. In contrast, feed pellets of Type C, in which the active ingredient is embedded in microspherules, exhibit significantly less active ingredient loss. After 2 months at 25° C., the loss is only about 1% and, at elevated temperature at 40° C., only about 11%. Even after 6 months, almost 80% of the active ingredient is still present in the case of Type C, whereas in the two other cases the active ingredient content falls below 10%.

That significant stabilisation of the active ingredient in feed pellets could in no way have been predicted, especially as the incorporation of microspherules in uncompressed feed does not result in any stabilisation. In uncompressed feed, unprotected valnemulin and valnemulin in microspherules behave in entirely the same manner and result in the same losses.

Note: At the date of this Application, this test has still not yet been completed; further data will be obtained in the coming months.

What is claimed is:

1. Polymeric matrix microspherules comprising an active ingredient comprising a compound of formula I,

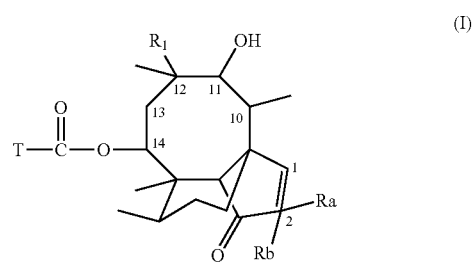

wherein $R_1$ is vinyl; there is a single bond between carbon atoms 1 and 2;

Ra and Rb are H, and

T is —$CH_2$—S—$(CH_2)_k$—$N(R_5)(R_6)$ wherein k is an integer from 2 to 5; and $R_5$ and $R_6$ are each independently of the other $C_{1-6}$alkyl;

or a physiologically tolerable acid addition salt or quaternary ammonium salt thereof;

wherein said microspherules have an average size of from about 1 μm to about 5000 μm, and whereby said compound of formula I, in solid or liquid form, is highly dispersed and embedded therein, wherein said polymeric matrix comprises methacrylic acid butyl ester, (2-dimethylaminoethyl)methacrylate and methyl methacrylate copolymer, and wherein the polymeric matrix microspherules stabilizes the active ingredient so that it withstands pellet preparation and provides storage-stability to the active ingredient, wherein storage-stability means that about 80% of the active ingredient remains present after storage for six months at 40° C.

2. A method of preparing polymeric matrix microspherules comprising an active ingredient comprising a compound of formula I,

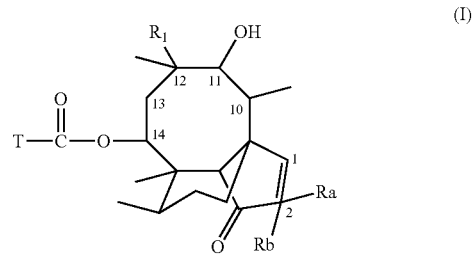

wherein $R_1$ is vinyl; there is a single bond between carbon atoms 1 and 2;

Ra and Rb are H, and

T is —$CH_2$—S—$(CH_2)_k$—$N(R_5)(R_6)$ wherein k is an integer from 2 to 5; and $R_5$ and $R_6$ are each independently of the other $C_{1-6}$alkyl;

or a physiologically tolerable acid addition salt or quaternary ammonium salt thereof;

wherein said microspherules have an average size of from about 1 μm to about 5000 μm, and whereby said compound of formula I, in solid or liquid form, is highly dispersed and embedded therein, and wherein the polymeric matrix microspherules stabilizes the active ingredient so that it withstands pellet preparation and provides storage-stability to the active ingredient, wherein storage-stability means that about 80% of the active ingredient remains present after storage for six months at 40° C., said method comprising:
(a) dissolving a polymer in an organic solvent, and optionally water, to form a polymer solution, whereby said polymer comprises methacrylic acid butyl ester, (2-dimethylaminoethyl)methacrylate and methyl methacrylate copolymer; and whereby said organic solvent has low affinity for paraffin oil or silicone oil and a dielectric constant of from about 10 to about 40;
(b) introducing said compound of formula I into said polymer solution with stirring, so that a first, organic phase, which is not miscible with paraffin oil or silicone oil, is formed;
(c) introducing said first, organic phase, with vigorous stirring, into a second, oily phase consisting of paraffin oil or silicone oil, and continued stirring of the resulting mixture until the microspherules containing said compound of formula I are formed on evaporation or removal of said organic solvent;
(d) isolating, and, optionally, washing and drying, of the microspherules.

\* \* \* \* \*